(12) United States Patent
Seapan et al.

(10) Patent No.: US 7,098,368 B2
(45) Date of Patent: *Aug. 29, 2006

(54) HYDROGENATION OF BIOCHEMICAL DERIVED 1,3 -PROPANEDIOL

(75) Inventors: Mayis Seapan, Landenberg, PA (US); George F. Diffendall, Wilmington, DE (US); Robert E. Trotter, Wilmington, DE (US); Tyler T. Ames, Wilmington, DE (US); F. Glenn Gallagher, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 64 days.

This patent is subject to a terminal disclaimer.

(21) Appl. No.: 10/839,655

(22) Filed: May 5, 2004

(65) Prior Publication Data

US 2004/0260125 A1 Dec. 23, 2004

Related U.S. Application Data

(60) Provisional application No. 60/468,212, filed on May 6, 2003.

(51) Int. Cl.
*C07C 29/74* (2006.01)
*C07C 29/88* (2006.01)
*C07C 29/90* (2006.01)
*C07C 27/26* (2006.01)

(52) U.S. Cl. ............ 568/868; 568/852; 568/854; 568/869; 435/132; 435/155; 435/157; 435/158; 435/159

(58) Field of Classification Search ........... 568/868, 568/852, 854, 869; 435/132, 155, 157, 158, 435/159
See application file for complete search history.

(56) References Cited

U.S. PATENT DOCUMENTS

| | | |
|---|---|---|
| 3,326,985 A | 6/1967 | Mason |
| 5,527,973 A | 6/1996 | Kelsey |
| 5,633,362 A | 5/1997 | Nagarajan et al. |
| 5,686,276 A | 11/1997 | Laffend et al. |
| 5,821,092 A | 10/1998 | Nagarajan et al. |
| 6,235,948 B1 | 5/2001 | Sunkara et al. |
| 2002/0007043 A1 | 1/2002 | Sunkara et al. |
| 2002/0010374 A1 | 1/2002 | Sunkara et al. |
| 2003/0082756 A1 | 5/2003 | Laffend et al. |

FOREIGN PATENT DOCUMENTS

| | | |
|---|---|---|
| DE | 1 025 852 | 3/1958 |
| DE | 3 917 645 | 12/1989 |
| EP | 657529 | 6/1995 |
| EP | 0 983 985 A | 3/2000 |
| WO | WO 01/47850 A | 7/2001 |

OTHER PUBLICATIONS

S. M. Ghoreishi et al., Characterization and Reduction of Chromophores in Pulp Mill Effluents, Sci. Iran., vol. 4(3):131–138, 1997.

H. O. House, Modern Synthetic Reactions—Catalytic Hydrogenation and Dehydrogenation, Second ed., W.A. Benjamin: Menlo Park, CA, pp. 1–15, 1972.

*Primary Examiner*—Elvis O. Price

(57) ABSTRACT

The invention discloses a hydrogenation process for removing impurities and controlling acid for use in downstream processing of biochemically-derived 1,3-propanediol. Preferably, the biochemically-derived 1,3-propanediol, before the contacting, has an initial color and, after the contracting, has a color that is lower than the initial color.

31 Claims, No Drawings

HYDROGENATION OF BIOCHEMICAL DERIVED 1,3-PROPANEDIOL

This application claims the benefit of U.S. Provisional Application No. 60/468,212, filed May 6, 2003, which is hereby incorporated herein by reference.

FIELD OF THE INVENTION

This invention relates to removal of color and color precursors from biochemically derived 1,3-propanediol by hydrogenation.

BACKGROUND OF THE INVENTION 1,3-Propanediol (also hereinafter termed "PDO") is a monomer useful in the production of a variety of polymers including polyesters, polyurethanes, polyethers, and cyclic compounds. Homo and copolyethers of polytrimethylene ether glycol (hereinafter termed "PO3G") are examples of such polymers. The polymers are ultimately used in various applications including fibers, films, etc.

Chemical routes to generate 1,3-propanediol are known. For instance, 1,3-propanediol may be prepared from:
1. ethylene oxide over a catalyst in the presence of phosphine, water, carbon monoxide, hydrogen and an acid (the "hydroformylation route");
2. the catalytic solution phase hydration of acrolein followed by reduction (the "acrolein route").

Both of these synthetic routes to 1,3-propanediol involve the intermediate synthesis of 3-hydroxypropionaldehyde (hereinafter also termed "HPA"). The HPA is reduced to PDO in a final catalytic hydrogenation step. Subsequent final purification involves several processes, including vacuum distillation. Hereinafter, the PDO from chemical processes is termed "chemical 1,3-propanediol" or "chemical PDO". Chemical PDO is from non-renewable resources, typically petrochemical products.

By contrast, biochemically or fermentatively produced 1,3-propanediol or PDO is, by definition, from renewable resources. Biochemical routes to 1,3-propanediol have been described that utilize feedstocks produced from biological and renewable resources such as corn feed stock. Such PDO is hereinafter referred to as "biochemical PDO", "bio-PDO" or "biochemically-derived PDO". For example, bacterial strains able to convert glycerol into 1,3-propanediol are found in e.g., in the species *Klebsiella, Citrobacter, Clostridium,* and *Lactobacillus*. The technique is disclosed in several patents, including, U.S. Pat. Nos. 5,633,362, 5,686,276, and, most recently, U.S. Pat. No. 5,821,092, all of which are incorporated herein by reference. In U.S. Pat. No. 5,821,092, Nagarajan et al., disclose inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Recombinant microorganisms are disclosed in U.S. Pat. No. 5,686,276, Laffend et al., that convert glucose (e.g., corn sugar) or other carbohydrates (other than glycerol and dihydroxyacetone) to glycerol and then to 1,3-propanediol. The process of the invention provided a rapid, inexpensive and environmentally responsible source of 1,3-propanediol monomer useful in the production of polyesters, polyethers, and other polymers.

Precipitations (e.g., with 1,2-propylene glycol, as well as carboxylates or other materials) have been used since the early 1980's to separate the colored and odiferous components from desired products (such as enzymes) to obtain purified preparations. Precipitating the high molecular weight constituents from the fermentor liquors, then bleaching these components with a reducing agent (DE3917645) is known. Alternately, microfiltration followed by nanofiltration to remove the residual compounds has also been found helpful (EP657529) where substances with a high molecular weight above the size of separation are held back. However, nanofiltration membranes become clogged quickly and can be quite expensive.

Various treatment methods are disclosed in the prior art to remove color precursors present in the PDO, however, the methods are laborious, expensive and increase the cost of the polymer. For instance, Kelsey, U.S. Pat. No. 5,527,973, discloses a process for providing a purified 1,3-propanediol that can be used as a starting material for low color polyester. That process has several disadvantages including the use of large equipment and the need for dilution with large quantities of water, which are difficult to remove from the product. Sunkara et al., U.S. Pat. No. 6,235,948, discloses a process for the removal of color-forming impurities from 1,3-propanediol by a preheating, preferably with heterogeneous acid catalysts such as perfluorinated ion exchange polymers. The catalyst is filtered off, and the 1,3-propanediol is then isolated, preferably by vacuum distillation. Preparation of polytrimethylene ether glycol from purified diol gave APHA values of 30–40, however, the molecular weight of the polymers were not reported.

The polyalkylene ether glycols are generally prepared by the acid-catalyzed elimination of water from the corresponding alkylene glycol or the acid-catalyzed ring opening of the alkylene oxide. For example, polytrimethylene ether glycol can be prepared by dehydration of 1,3-propanediol or by ring opening polymerization of oxetane using soluble acid catalysts. Methods for making PO3G from the glycol, using sulfuric acid catalyst, are fully described in U.S. patent application publication Nos. 2002/0007043A1 and 2002/0010374A1, all of which are incorporated herein by reference. The polyether glycol prepared by the process is purified by the methods known in the art. The purification process for polytrimethylene ether glycol typically comprises (1) a hydrolysis step to hydrolyze the acid esters formed during the polymerization (2) water extraction steps to remove the acid catalyst, unreacted monomer, low molecular weight linear oligomers and oligomers of cyclic ethers, (3) a base treatment, typically with a slurry of calcium hydroxide, to neutralize and precipitate the residual acid present, and (4) drying and filtration of the polymer to remove the residual water and solids.

It is well known that the polytrimethylene ether glycol produced from the acid catalyzed polycondensation of 1,3-propanediol has quality problems, in particular, the color is not acceptable to the industry. The polymer quality is in general dependent on the quality of the raw material, PDO. Besides the raw material, the polymerization process conditions and stability of the polymer are also responsible for discoloration to some extent. Particularly in the case of polytrimethylene ether glycol, the polyether diols tend to have light color, a property that is undesirable in many end-uses. The polytrimethylene ether glycols are easily discolored by contact with oxygen or air, particularly at elevated temperatures, so the polymerization is effected under a nitrogen atmosphere and the polyether diols are stored in the presence of inert gas. As an additional precaution, a small concentration of a suitable antioxidant is added. Preferred is butylated hydroxytoluene (BHT, 2.6-dit-butyl-4-methylphenol) at a concentration of about 100–500 microg/g (micrograms/gram) polyether.

Also, attempts have been made to reduce the color of polytrimethylene ether glycols by conventional means without much success. For instance, Morris et al., U.S. Pat. No. 2,520,733, notes the peculiar discoloration tendency for the polytrimethylene ether glycol from the polymerization of PDO in the presence of acid catalyst. The many methods they tried that failed to improve the color of polytrimethylene glycols included the use of activated carbons, activated aluminas, silica gels, percolation alone, and hydrogenation alone. Consequently, they developed a process for the purification of polyols prepared from 1,3-propanediol in the presence of acid catalyst (2.5 to 6% by weight) and at a temperature from about 175° C. to 200° C. This purification process involves percolation of the polymer through Fuller's earth followed by hydrogenation. This extensive purification process gave a final product that was light yellow in color, in fact, this procedure yielded polytrimethylene ether glycol (Example XI therein) for which the color was only reduced to an 8 Gardner color, a quality corresponding to an APHA value of >300 and totally inadequate for current requirements.

Mason in U.S. Pat. No. 3,326,985 discloses a procedure for the preparation of polytrimethylene ether glycol of molecular weights in the range of 1200–1400 possessing improved color by vacuum stripping, under nitrogen, polytrimethylene ether glycol of lower molecular weight. The color levels, however, are not quantified and would not have approached the above requirement.

Catalytic hydrogenation is the reaction of a compound with hydrogen in the presence of a catalyst. Hydrogenation has been used to remove color-causing compounds in the production of certain products from wastewater streams of the kraft pulp mill process (Ghoreishi et al., Characterization and Reduction of Chromophores in Pulp Mill Effluents. *Sci. Iran.* 4(3):131–138 (1997)). A variety of substances are poisons for hydrogenation catalysts; the most commonly encountered being mercury, divalent sulfur compounds, and, to a lesser degree, amines (H. O House, *Modern Synthetic Reactions,* Second ed., W. A. Benjamin: Menlo Park, Calif., pp 1–15 (1972)).

SUMMARY OF THE INVENTION

Disclosed is a process comprising contacting biochemically-derived 1,3-propanediol with hydrogen in the presence of a hydrogenation catalyst. Preferably, the biochemically-derived 1,3-propanediol, before the contacting, has an initial color and, after the contacting, has a color that is lower than the initial color.

DETAILED DESCRIPTION OF THE INVENTION

Unless stated otherwise, all percentages, parts, ratios, etc., are by weight. Trademarks are shown in upper case.

Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

The present invention is directed towards a hydrogenation process for biochemically-derived PDO. In accordance with a first aspect, a process comprises contacting biochemically-derived 1,3-propanediol with hydrogen in the presence of a hydrogenation catalyst. Preferably, the biochemically-derived 1,3-propanediol, before the contacting has an initial color and, after the contacting, has a color that is lower than the initial color.

By the terms "remove" or "removal", as applied to color and color precursors, is meant a chemical conversion by hydrogenation. Chemicals that cause color, or have the potential to cause color in subsequent processing, are "removed", i.e., converted into chemicals that are not colored and do not have the potential to cause color in subsequent processing.

By the term "color" is meant the existence of visible color that can be quantified using a spectrocolorimeter in the range of visible light, using wavelengths of approximately 400–800 nm, and by comparison with pure water. Color precursors in chemical PDO are not visible in this range, but subsequently react to give compounds that contribute color in the polyester, polyether glycol, and polyester diols during polymerization or isolation. While not wishing to be bound by theory, we believe color precursors include trace amounts of impurities comprising olefinic bonds, acetals and other carbonyl compounds, peroxide-forming compounds, etc. At least some of these impurities have UV absorption that may be detected by such methods as UV spectroscopy (Test Method 4 below) or peroxide titration, etc.

"Crude PDO Solution" refers to an aqueous solution of biochemically-derived 1,3-propanediol and impurities, wherein the weight percent of 1,3-propanediol is at least 5% and the weight % of water can be as low as 0%. The terms "organic materials" or "organic impurities" refer to the contaminants in the solution containing carbon.

The biochemically-derived PDO color quality can be measured by a UV/VIS spectrophotometer as described in Test Method 4 below.

Biochemically-derived PDO contains impurities that are either color compounds or are color precursors that form color compounds upon further processing, for example, during thermal processing in subsequent polymerization or distillation steps. These compounds give color to the biochemically-derived PDO and the polymers and polymeric objects made from biochemically-derived PDO. Polymers made from biochemically-derived PDO include polyethers, polyesters, and polyether esters.

Hydrogenation has been found an effective, economical way to convert these impurities to compounds that are colorless, and which no longer have the potential to form color during subsequent processing.

Hydrogenation is achieved by contacting the biochemically-derived PDO with hydrogen in the presence of a hydrogenation catalyst. The catalyst is comprised of at least one element of Group VIII of the periodic table. Preferably, the catalyst is at least one of Ni, Co, Ru, Rh, Pd, Ir and Pt, with or without various promoters. Various mixed metal oxides such mixed copper, chromium, and zinc oxides are also effective catalysts for color removal. Hydrogenation catalysts are well known in the art and are extensively covered in "*Handbook of Heterogeneous Catalytic Hydrogenation for Organic Synthesis*" by Shigeo Nishimuru, John Wiley (2001).

The catalyst may be a porous metal structure or supported on a substrate. The catalyst support could be from any support material known in the art, such as at least one of carbon, alumina, silica, titania, silica-alumina, silica-titania, titania-alumina, clays, aluminosilicates, water insoluble salts of calcium, barium, barium sulfate, calcium carbonate, strontium carbonate, and compounds and combinations thereof. The catalyst may have various shapes or sizes, ranging from a fine powder to granules, tablets, pellets, extrudates, or other structured supports. The metal catalyst comprises at least one of RANEY nickel and RANEY cobalt catalysts which is optionally modified with at least one of iron, molybdenum, chromium, palladium, zinc or other modifying elements, or catalysts made as dispersions of these elements, or supported catalysts from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica, mixed copper and zinc oxides, and mixed copper and chromium oxides. An example of the preferred catalyst is nickel, which may be in the form of a RANEY catalyst (which may be doped with other catalytically active metals) or extrudates supported on silica/alumina.

Hydrogenation may be carried out in various gas/liquid/solid-contacting reactors known in the art. These reactors may operate in batch, semi-batch, and flow mode, using suspended or fixed bed catalysts. An industrially advantageous reactor uses a packed bed of catalyst wherein the liquid and gas flow co-currently or counter-currently, in an up-flow or down-flow (trickle-bed) mode of operation.

The variability of the UV spectra of the crude biochemically-derived PDO solution depends on the process that generated the crude PDO and also on the effectiveness of the purification steps. The extent of color reduction by hydrogenation depends on the initial color level of the crude PDO solution. For a given color level in the crude PDO solution, the desired color reduction can be achieved by selecting suitable operating conditions for hydrogenation Hydrogenation temperature affects the conversion of color or color-precursor compounds. Temperatures in the range of about 25°–250° C. can reduce color. Color reduction is faster at higher temperatures. A proper combination of contact time and temperature can achieve a desired color improvement at temperatures as low as about 25° C. While effective color reduction can be achieved in the range of about 25°–250° C., the preferred temperature ranges for PDO is about 80°–130° C., with a more preferred range of about 100°–120° C. LHSV values (LHSV=Liquid Hourly Space Velocity, units reciprocal hours, $h^{-1}$) in flow reactors are dependent on the temperature used, and should be maximized. A preferred LHSV is greater than about 0.01 $h^{-1}$. A more preferred LHSV is greater than about 1.0 $h^{-1}$, and a most preferred LHSV is greater than about 10 $h^{-1}$.

Hydrogen consumption is generally very low and depends on the level of impurities present in the crude biochemically-derived PDO. Generally, hydrogen consumption is within the range of hydrogen solubility in the crude liquid. With the proper selection of temperature and contact time, adequate conversion can be achieved at slightly above atmospheric pressures. Above this level, an additional increase in pressure has minimal effect on the extent of color removal. Color reductions can be achieved at pressures from about ambient to 1000 psig (7000 kPa), with 200–600 psig (1480–4240 kPa) being the preferred range of pressure. A more preferred range is 300–500 psig (2170–3550 kPa). Psig denotes "pounds per square inch gauge".

The ratio of hydrogen to biochemically-derived PDO feed rate does not have a significant effect on the conversion above the stoichiometric required level of hydrogen. Effective color reductions can be achieved at 0.05–100 standard $cm^3$ of hydrogen per gram of crude PDO. The preferred range is 0.5–2 standard $cm^3$ of hydrogen and a more preferred range is 0.5–1 standard $cm^3$ of hydrogen per gram of crude PDO.

As noted above, according to one aspect of the present invention, the color of the 1,3-propanediol, after hydrogenation, is lower than the initial color of the chemical PDO. Preferably, the color, after hydrogenation, is less than about 10 APHA. More preferably, the color of the chemical PDO, after hydrogenation, is less than about 5 APHA, measured according to Test Method 1, below.

The level of color precursors in biochemically-derived PDO as measured by UV spectra is also lower after hydrogenation. Preferably the UV absorption at 270 nm after hydrogenation is less than about 0.02 and more preferably is less than about 0.002, measured according to Test Method 4, below. In accordance with another aspect in accordance with the present invention, UV absorption of the chemical 1,3-propanediol, after hydrogenation, is reduced by at least about 50%. More preferably, the UV absorption is reduced by at least about 60%, most preferably, by at least about 70%.

In accordance with another aspect, the color of the biochemically-derived 1,3-propanediol, after hydrogenation, has a color value less than about 15 APHA when treated with 1 wt % sulfuric acid at 170° C. for 10 minutes.

According to another aspect, the hydrogenated 1,3-propanediol made in accordance with the present invention is contacted with suitable catalyst to make polyether diol or polyester diol. Suitable catalysts for this purpose are known. Preferably, the polymer so produced, has a APHA color of less than about 50, preferably, less than 30, and a molecular weight of about 250–5000, preferably about 500–4000, more preferably, about 1000–3000.

According to a further aspect in accordance with the present invention, a composition comprises (i) biochemically-derived 1,3-propanediol having color and (ii) hydrogenation catalyst (as already described herein), wherein the biochemically-derived 1,3-propanediol has a APHA color of less than about 10. Preferably, the APHA color is less than about 5 APHA.

The amount of catalyst is, preferably, the minimum amount sufficient to effect the hydrogenation, determination of which is considered to be well within the skill of the art. As is well known to those skilled in the art, the amount of catalyst is affected by the activity of the catalyst and the presence in the composition of chemicals that reduce the activity of, or poison, the catalyst. The amount of catalyst could be as low as about 0.05% of the composition, or 0.01%, or 0.005% or even 0.001% thereof. Preferably, the hydrogenation catalyst is used in an amount not exceeding about 20% of the composition. More preferably, the hydrogenation catalyst is used in an amount not exceeding about 5% of the composition and most preferably, the hydrogenation catalyst is used in an amount not exceeding about 2% of the composition.

Materials, Equipment, and Test Methods

The biochemically-derived 1,3-propanediol is from E.I. du Pont de Nemours and Company and chemical 1,3-propanediol is either from E. I. du Pont de Nemours and Company (Wilmington Del.), Aldrich (Milwaukee Wis.), or from other commercial sources.

Test Method 1. Color Measurement.

A Hunterlab ColorQuest Spectrocolorimeter (Reston, Va.) was used to measure the PDO and polymer color. Color numbers are measured as APHA values (Platinum-Cobalt System) according to ASTM D-1209. The "b*" color of PDO is calculated from the UV/VIS spectra and computed by the instrument. Color is commonly expressed in terms of Hunter numbers which correspond to the lightness or darkness ("L") of a sample, the color value ("a*") on a red-green scale, and the color value ("b*") on a yellow-blue scale. In the context of this invention, the "b*" color value is preferably near 0.

Test Method 2. Molecular Weight Determination.

The polymer molecular weights are calculated from their hydroxyl numbers obtained by titration (Test Method 3).

Test Method 3. Hydroxyl Number.

The hydroxyl number was determined according to ASTM E222

Test Method 4. UV Absorption

The chemical PDO color quality was measured by a UV/VIS spectrophotometer. Specifically, the broad UV absorption peak at around 270–280 nm correlates strongly with the presence of color precursors in the PDO and color in the polymers made therefrom. All the UV analyses were measured using a HP 8453 UV/VIS (Hewlett-Packard, Palo Alto, Calif.) spectrophotometer after diluting the chemical PDO to a 20% concentration by volume with water. The results are reported at this 20% dilution. UV absorption at about 193 and 230 nm have less correlation with color precursors.

EXAMPLES

It should be understood that the following examples are given by way of illustration only.

General Methods

The material and methods suitable for hydrogenation are well known in the art. In the Examples that follow, shaker-tube and up-flow fixed bed tubular reactors were used that operated in batch or flow modes using fine powder, granular, and extrudate catalysts.

The PDO color quality was measured by a UV/VIS spectrophotometer. All the UV analyses were done using an HP 8453 UV/VIS spectrophotometer at 20% dilution with water and reported as such. The impurities in PDO were measured with gas chromatography. All GC analyses were done with an Agilent 6890 Gas Chromatograph using a 7673 series auto-injector, 5973N Mass Selective Detector, HP-INNOWax polyethyleneglycol capillary column, 30 m long, 250 micrometer diameter, 0.25 micrometer film thickness. The initial temperature was 100° C., which increased at 10 C/min rate to 193° C., followed by an increase in temperature to 250° C. at 40° C./min and held for 12 min.

The sulfur was analyzed by a Perkin-Elmer 3300RL Inductively Coupled Plasma (ICP) analyzer. The acidity of PDO was analyzed with a Beckman Model 350 pH meter. The pH is measured in two ways: neat and in 50/50 dilution with water.

Generic Protocol for Bioproduction of 1,3-Propanediol

A previously purified biochemically-derived 1,3-propanediol (PDO) was used as the starting material. The PDO had been prepared in a fermentation process starting from dextrose and purified in various steps including but not limited to filtration, ion exchange, evaporation, spray-drying, carbon adsorption, chromatographic separation, and various stages of distillation. Depending on the elements of the fermentation process and the particular purification steps used in each case, the crude PDO solution used in the following examples contained various impurities. Each set of examples uses a biochemically-derived PDO made via a different combination of fermentation and/or pre-cleaning processes and are designated as Cases A, B, C.

Case A: Use of Invention After Four-Step Distillation of Aqueous Mixture.

In this series of examples (1–9), a PDO solution purified in various steps of filtration, adsorption, ion-exchange and evaporation followed by four stages of distillation was used as the feed to hydrogenation. GC analysis of this feed showed over 22 unknown impurities, comprising over 0.13% of the area counts. The UV/VIS spectrum of the crude feed had three wide absorption bands with maxima around 200, 220, and 270–280 nm.

Examples 1–8

In these examples, biochemically-derived PDO described in Case A was hydrogenated in a shaker tube with RANEY 2400 Nickel slurry catalyst (Cr and Fe promoted Ni) at the various operating conditions summarized in Table 1. In all cases, 200 g of PDO was placed in a 400 mL stainless steel shaker tube with the designated amount of the catalyst. The shaker tube was purged with nitrogen, heated to the specified temperature, and pressurized with hydrogen to the designated pressure. The reactor was kept shaking for the specified time, then cooled and depressurized. The quality of the hydrogenated product was determined with GC and UV/VIS as described above. Table 1 shows the reduction in the UV absorption at 280 nm.

TABLE 1

Conditions and results of Examples 1–8

| Example | Temp. C. | Pressure Psia | Cat. Wt % | Time hr. | UV-280 A.U. |
|---|---|---|---|---|---|
| Feed | | | | | 1.58 |
| 1 | 80 | 400 | 0.05 | 1 | 0.64 |
| 2 | 100 | 400 | 0.05 | 1 | 0.65 |
| 3 | 80 | 800 | 0.05 | 1 | 0.99 |
| 4 | 100 | 800 | 0.05 | 2 | 0.46 |
| 5 | 100 | 100 | 0.125 | 0.25 | 1.28 |
| 6 | 100 | 100 | 0.125 | 1 | 1.08 |
| 7 | 120 | 400 | 0.125 | 1 | 0.53 |
| 8 | 140 | 400 | 0.125 | 1 | 0.42 |

Color removal improves with temperature, contact time, and amount of catalyst. In Example 1, hydrogenation completely eliminated nine of the twenty-two impurities in the crude biochemically-derived PDO solution and reduced the concentration of five, formed six new compounds, and increased the concentration of three existing impurities. The formed impurities were either much lighter or much heavier than PDO, and therefore could be easily removed by distillation. These compounds with their designated retention times are shown in Table 2. In Examples 2–8, similar changes in the impurities were observed, though not to the same extent, depending on the severity of the operating conditions.

TABLE 2

Changes in the Impurities of biochemically-derived PDO upon Hydrogenation
Example 1
Composition Change in Hydrogenation

| Retention Time | Change |
|---|---|
| 1.282 | disappeared |
| 1.306 | Formed |
| 1.439 | Formed |
| 2.246 | disappeared |
| 3.253 | disappeared |
| 4.191 | disappeared |
| 4.270 | Formed |
| 5.285 | disappeared |
| 5.674 | unchanged |
| 5.760 | Increased |
| 5.902 | Reduced |
| 6.104 | unchanged |
| 6.900 | unchanged |
| 7.333 | unchanged |
| 7.490 | Formed |
| 8.058 | disappeared |
| 8.567 | disappeared |
| 8.828 | disappeared |
| 9.206 | unchanged |
| 9.278 | unchanged |
| 9.616 | Formed |
| 9.743 | Reduced |
| 9.847 | unchanged |
| 10.257 | Increased |
| 10.386 | unchanged |
| 10.620 | Formed |
| 10.669 | Reduced |
| 10.827 | Increased |
| 11.395 | disappeared |

Example 9

Following the shaker tube tests of Examples 1–8, 11.8 kg of the PDO solution from Example 1 was charged in a 5 gal autoclave reactor with 24 g of RANEY 2400 Nickel slurry catalyst. The mixture was hydrogenated at 400 psig and 120° C. for 4 h. The process was repeated three times and the products were combined and distilled in two pilot scale distillation columns to remove the lights and heavies. The final product had a UV-270 below 0.3 AU. This purified biochemically-derived PDO was polymerized to form poly-trimethylene-terephthalate that was clearly colorless with a b*-color of 0.33. The PDO without this hydrogenation and distillation process produced a polymer with a b*-color over 1.2, with a visible yellow color. The pH of the PDO before hydrogenation was 4.6; after hydrogenation the pH improved to 6.8.

Case B. Use of Invention on Crude Biochemically-Derived 1,3-Propanediol (Before Distillation)

As a process simplification, a more crude biochemically-derived 1,3-propanediol was used in a second series of tests. This 1,3-propanediol was also prepared in the fermentation process described above, starting from dextrose and purified in various steps of filtration, ion exchange, and evaporation but was distilled in only two distillation columns instead of four. GC analysis of this feed showed over 40 unknown impurities, comprising about 1% of the area counts. The UV/Vis absorption was quite strong, such that after diluting to 20%, its UV-270 absorption was 3.4 AU.

Example 10

12.5 kg of the crude PDO solution described in Case B above, was charged in a 5 gal autoclave reactor with 52 g of RANEY® Nickel slurry catalyst. The mixture was hydrogenated at 400 psig for one h at 120° C. followed by 4 h at 130° C. Three additional batches were similarly hydrogenated and the products were combined and distilled in two pilot scale distillation columns to remove the lights and heavies. The final product had a UV-270 below 0.1 AU. This purified biochemically-derived 1,3-propanediol was polymerized to form clearly colorless poly-trimethylene-terephthalate with a b*-color of 0.88. The pH of the PDO before hydrogenation was 4.7; after hydrogenation the pH improved to 6.6.

Case C. Use of Invention on Crude Biochemically-Derived 1,3-Propanediol, with Modified and Improved Pre-Purification By changes in the fermentation and purification process conditions, several crude biochemically-derived PDO solutions with improved quality were obtained. These PDO solutions were hydrogenated in an up-flow, packed bed reactor under various conditions. The reactor was a ¾ in. diameter and 20 in. long stainless steel-jacketed reactor. Hot oil flowing in the jacket maintained a constant temperature in the reactor. The reactor was packed with desired lengths of catalyst supported between two layers of inert packing. PDO and hydrogen entered into the reactor from the bottom at the desired pressure. They passed through the reactor in an upflow mode, separating in a separator downstream of the reactor. Various catalysts were tested including a commercial granular RANEY 2486 nickel (Cr and Fe promoted Ni) and a commercial nickel on silica/alumina catalyst (Sud-Chemie C-28-CDS) containing 50–60% Ni, and a commercial ruthenium on carbon supported catalyst (Synetix PRI-CAT HTC-400 RP).

Examples 11–20

In these examples, a biochemically-derived PDO described as Case C was hydrogenated with three commercially available catalysts at various operating conditions. The operating conditions of each example and the results are shown in Table 3. Color removal improves with temperature and increased contact time or reduced space velocity. Pressure has minimal effect on color removal. Sulfur is completely removed in all cases where it was measured and pH of the product improved from an acidic to a more neutral range.

TABLE 3

| Example | Catalyst | LHSV, 1/h | $H_2$/PDO, scc/g | Temp. ° C. | Press. psig | Product UV | S ppm | pH |
|---|---|---|---|---|---|---|---|---|
| Feed | | | | | | 1.52 | 13 | 5.7 |
| 11 | RANEY Ni | 4 | 21.3 | 120 | 400 | 0.35 | | |
| 12 | RANEY Ni | 4 | 21.3 | 120 | 650 | 0.32 | | |
| 13 | Ru/C | 4 | 21.3 | 120 | 400 | 0.33 | | |

TABLE 3-continued

| Example | Catalyst | LHSV, 1/h | H$_2$/PDO, scc/g | Temp. °C. | Press. psig | Product UV | S ppm | pH |
|---|---|---|---|---|---|---|---|---|
| 14 | Ni/SiO$_2$—Al2O$_3$ | 4 | 21.3 | 80 | 400 | 0.55 | | |
| 15 | Ni/SiO$_2$—Al$_2$O$_3$ | 4 | 21.3 | 100 | 400 | 0.47 | | |
| 16 | Ni/SiO$_2$—Al$_2$O$_3$ | 4 | 21.3 | 60 | 400 | 0.74 | | |
| 17 | Ni/SiO$_2$—Al$_2$O$_3$ | 4 | 21.3 | 40 | 400 | 0.87 | | |
| 18 | Ni/SiO$_2$—Al$_2$O$_3$ | 3.8 | 22.4 | 120 | 400 | 0.32 | | |
| 19 | Ni/SiO$_2$—Al$_2$O$_3$ | 1.9 | 22.4 | 120 | 400 | 0.35 | 0 | 7.5 |
| 20 | Ni/SiO$_2$—Al$_2$O$_3$ | 1.27 | 22.4 | 120 | 400 | 0.15 | 0 | 6.7 |

What is claimed is:

1. A process comprising contacting a mixture comprising organics and biochemically-derived 1,3-propanediol with hydrogen in the presence of a hydrogenation catalyst.

2. The process of claim 1, wherein the biochemically-derived 1,3-propanediol, before the contacting, has an initial color and, after the contacting, has a color that is lower than the initial color.

3. The process of claim 2, wherein the biochemically-derived color of the 1,3-propanediol, after hydrogenation, is less than about 10 APHA.

4. The process of claim 2, wherein the biochemically-derived color of the 1,3-propanediol, after hydrogenation, is less than about 5 APHA.

5. The process of claim 2, wherein the color of 1,3-propanediol, after hydrogenation, has a color value less than about 15 APHA when treated with 1 wt % sulfuric acid at 170 degrees C. for 10 minutes.

6. The process of claim 1, wherein the catalyst comprises at least one element of Group VIII of the Periodic Table or a metal oxide.

7. The process of claim 6 wherein the hydrogenation catalyst is supported on a support comprised of at least one of carbon, alumina, silica, titania, silica-alumina, silica-titania, titania-alumina, clays, aluminosilicates, water insoluble salts of calcium, barium, barium sulfate, calcium carbonate, strontium carbonate, and compounds and combinations thereof.

8. The process of claim 1, wherein the catalyst comprises at least one of RANEY nickel and RANEY cobalt catalyst which is optionally modified with at least one of iron, molybdenum, chromium, palladium, zinc or other modifying elements, or catalysts made as dispersions of these elements, or supported catalysts from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica, mixed copper oxide, zinc oxides, and chromium oxides.

9. The process of claim 1, wherein the contacting is conducted at a temperature of about 25–250° C.

10. The process of claim 9, wherein the contacting is conducted at a temperature of about 80–130° C.

11. The process of claim 10, wherein the contacting is conducted at a temperature of about 100–120° C.

12. The process of claim 9, wherein the contacting is conducted at an LHSV that is at greater than about 0.01 h$^{-1}$.

13. The process of claim 12, wherein the contacting is conducted at an LHSV that is greater than about 1.0 h$^{-1}$.

14. The process of claim 13, wherein the contacting is conducted at an LHSV that is greater than about 10 h$^{-1}$.

15. The process of claim 12, wherein the contacting is conducted at a pressure of about ambient to about 1000 psig (7000 kPa).

16. The process of claim 15, wherein the contacting is conducted at a pressure of about 200–600 psig (1480–2860 kPa).

17. The process of claim 16, wherein the contacting is conducted at a pressure of about 300–500 psig.

18. The process of claim 15, wherein the amount of hydrogen contacted with the 1,3-propanediol is about 0.05–100 standard cm$^3$ per gram of 1,3-propanediol.

19. The process of claim 18, wherein the amount of hydrogen is about 0.5–2 standard cm$^3$ per gram of 1,3-propanediol.

20. The process of claim 19, wherein the amount of hydrogen is about 0.5–1 standard cm$^3$ per gram of 1,3-propanediol.

21. The process of claim 2, wherein the UV absorption of the 1,3-propanediol is reduced by at least about 50%.

22. The process of claim 2, wherein the UV absorption of the 1,3-propanediol is reduced by at least about 60%.

23. The process of claim 2, wherein the UV absorption of the 1,3-propanediol is reduced by at least about 70%.

24. The process of claim 2, wherein the UV absorption of the 1,3-propanediol, after hydrogenation, at 270 nm is less than about 0.02.

25. The process of claim 2, wherein the UV absorption of the 1,3-propanediol, after hydrogenation, at 270 nm is less than about 0.002.

26. A composition comprising: (i) biochemically-derived 1,3-propanediol having color and (ii) hydrogenation catalyst, wherein the biochemically-derived 1,3-propanediol has a APHA color of less than about 10.

27. The composition of claim 26, wherein the biochemically-derived 1,3-propanediol has a APHA color of less than about 5.

28. The composition of claim 26, wherein the catalyst comprises an element of Group VIII of the Periodic Table or a metal oxide.

29. The composition of claim 28, wherein the catalyst is supported by at least one of carbon, alumina, silica, silica-alumina, silica-titania, titania, titania-alumina, barium sulfate, calcium carbonate, strontium carbonate, compounds thereof, and combinations thereof.

30. The composition of claim 29, wherein the catalyst is at least one of RANEY nickel and RANEY cobalt catalysts which is optionally modified with iron, molybdenum, chromium, palladium, zinc or other modifying elements, or catalysts made as dispersions of these elements, or supported catalysts from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica, mixed copper oxide, zinc oxides, and chromium oxides.

31. The composition of claim 26, containing about 2%–20% catalyst.

* * * * *